US009649278B2

(12) United States Patent
Read et al.

(10) Patent No.: US 9,649,278 B2
(45) Date of Patent: May 16, 2017

(54) INJECTION-MOLDED DOSAGE FORM

(71) Applicant: Dow Global Technologies LLC, Midland, MI (US)

(72) Inventors: Michael D. Read, Midland, MI (US); Karen A. Coppens, Midland, MI (US); Mark J. Hall, Gaylord, MI (US); Jin Zhao, Midland, MI (US)

(73) Assignee: Dow Global Technologies LLC

( * ) Notice: Subject to any disclaimer, the term of this patent is extended or adjusted under 35 U.S.C. 154(b) by 125 days.

(21) Appl. No.: 14/350,535

(22) PCT Filed: Oct. 9, 2012

(86) PCT No.: PCT/US2012/059323
§ 371 (c)(1),
(2) Date: Apr. 8, 2014

(87) PCT Pub. No.: WO2013/055668
PCT Pub. Date: Apr. 18, 2013

(65) Prior Publication Data
US 2014/0271833 A1    Sep. 18, 2014

Related U.S. Application Data

(60) Provisional application No. 61/546,242, filed on Oct. 12, 2011.

(51) Int. Cl.
*A61K 9/48* (2006.01)
*C08L 1/28* (2006.01)
*C08L 5/00* (2006.01)

(52) U.S. Cl.
CPC .......... *A61K 9/4816* (2013.01); *A61K 9/4833* (2013.01); *C08L 1/28* (2013.01); *C08L 5/00* (2013.01); *A61K 9/4883* (2013.01)

(58) Field of Classification Search
CPC .. A61K 9/4816; A61K 9/4833; A61K 9/4883; C08L 5/00; C08L 1/28
See application file for complete search history.

(56) References Cited

U.S. PATENT DOCUMENTS

| 2,526,683 A | 10/1950 | Murphy |
| 4,576,284 A | 3/1986 | Wittwer et al. |
| 4,645,812 A | 2/1987 | Maier |
| 4,738,724 A | 4/1988 | Wittwer et al. |
| 4,738,817 A | 4/1988 | Wittwer et al. |
| 4,790,881 A | 12/1988 | Wittwer et al. |
| 2003/0104047 A1 | 6/2003 | Chen et al. |
| 2005/0175687 A1 | 8/2005 | McAllister et al. |
| 2008/0103206 A1* | 5/2008 | Swann ................. A61K 31/167 514/570 |
| 2009/0074944 A1 | 3/2009 | Xie et al. |
| 2009/0110721 A1* | 4/2009 | McAllister ............. A61J 3/071 424/451 |
| 2009/0148518 A1 | 6/2009 | Brown et al. |
| 2010/0209480 A1* | 8/2010 | Altenburger .......... A61K 9/209 424/443 |
| 2011/0142925 A1* | 6/2011 | Scott .................... A61K 9/2866 424/451 |

FOREIGN PATENT DOCUMENTS

| CN | 1720903 | 1/2006 |
| EP | 0504870 | 9/1992 |
| JP | 1972003547 | 2/1972 |
| WO | 2005089726 | 9/2005 |
| WO | 2008086804 | 7/2008 |
| WO | 2009087483 A2 | 7/2009 |

OTHER PUBLICATIONS

Analytical Chemistry, vol. 51, 13, 1979, Hodges et al: Determination of Alkoxyl Substitution in Cellulose Ethers by Zeisel-Gas Chromatography.

* cited by examiner

*Primary Examiner* — Hasan Ahmed

(57) ABSTRACT

An injection-molded shell of a dosage form of good quality is producible by a) providing a composition comprising i) from 25 to 90 weight percent of ethylcellulose, ii) from 7.5 to 60 weight percent of a polysaccharide or polysaccharide derivative being different from ethylcellulose, and iii) from 2.5 to 50 weight percent of at least one component being different from polysaccharides and polysaccharide derivatives, based on the total weight of the composition, with the proviso that the composition comprises zero or not more than 10 weight percent of gelatin and zero or not more than 10 weight percent of a polymer comprising homo- or copolymerized acrylic acid, homo- or copolymerized methacrylic acid, a homo- or copolymerized acrylate or a homo- or copolymerized methacrylate, and b) subjecting the composition to shearing and heat to plasticize the composition and injection-molding the plasticized composition into a three-dimensional shell of a dosage form.

17 Claims, No Drawings

INJECTION-MOLDED DOSAGE FORM

FIELD

This invention relates to injection-molded dosage form having a cavity for an active ingredient, such as capsules.

INTRODUCTION

Various types of dosage forms, such as pharmaceutical dosage forms, are known for oral dosing. Capsules are well-known dosage forms that normally consist of a shell filled with one or more specific substances including active ingredients. The shell may be a soft or a hard stable shell comprising film-forming polymer(s) such as gelatin, modified starches or modified celluloses. Hard capsules are generally manufactured by using a dip molding process. U.S. Pat. No. 2,526,683 discloses a process for preparing methylcellulose medicinal capsules by a dip coating process. The process consists of dipping a capsule forming pin pre-heated to 40° C.-85° C. into an aqueous solution of methylcellulose maintained at a temperature below the temperature where gelation begins, withdrawing the pins and placing the pins in ovens at temperatures above the gelation temperature and drying the film. When the hot pins are dipped into the aqueous methylcellulose solution, the composition gels on the surface of the pin and as the pin is withdrawn, a film of gelled liquid of a certain thickness is formed on the pin. The pin is typically placed in the oven to dry. This technique is conventionally named "thermogelation". The dry capsule is then stripped, cut to size and the body and caps are fitted together.

While this well-established technology has many advantages, it also has certain limitations. The aqueous solution of methylcellulose needs to have a viscosity within a relatively narrow range and needs to be consistent batch to batch to be able to produce capsules of a uniform thickness. Also, the wall thickness of the capsule shell depends on the viscosity and solids content of the methylcellulose solution and cannot be increased beyond a certain thickness in one dipping step. If walls of higher thickness are desired, multiple dipping steps and drying cycles are needed, which is time-consuming and not economically viable. Moreover, the evaporation of the water during the drying step can lead to imperfections in the capsule shell.

U.S. Pat. No. 4,790,881 discloses a moldable non-gelatin containing hydrophilic polymer composition containing between 5 and 25% water. The hydrophilic polymer is heated with said water while maintaining the predetermined water content to form a melt, and the hydrophilic polymer in water mixture is heated above its glass transition temperature and above its melting point to dissolve the melt in the water. The heated composition is formed to capsules by an injection molding process. However, the melting and the glass transition temperature are above 100° C. which makes the control of the exact water content quite difficult. As indicated in the U.S. Pat. No. 4,790,881, maintenance of precise water content of the polymer is essential for proper operation at the desired speeds.

To address the problem of imperfections in capsule shells, US Patent Application Publication No. 2003/0104047 discloses a method for the manufacturing of non-gelatin hard capsule shells. The shell is made by a heat-melting method which involves adding a capsule forming composition (preferably in powdery form) in a mold, heating the mold and inserting a pre-heated capsule-forming pestle into the mold to coat the melted capsule forming composition onto the pestle, and withdrawing the heated pestle from the heated mold so that the coated capsule forming composition can be further cooled, dried and removed from the pestle. This method has the advantages over a conventional "dip molding method" for not requiring the capsule forming composition to be pre-dissolved in solution so that no solvent needs to be evaporated for hardening and drying the capsule shell on the pestle. However, also in this process the melted capsule forming composition needs to have a viscosity within a relatively narrow range to be able to produce capsule shells of a uniform thickness or weight on the pestle.

US Patent Application Publication No. 2005/0175687 relates to polymeric compositions suitable for injection molding of single or multi-component pharmaceutical dosage forms. In one aspect a composition is disclosed which comprises from 20 to 70 weight-% of Eudragit 4135F, from 20 to 70 weight-% of a hydroxypropyl cellulose derivative, 0 to 30 weight-% of a dissolution-modifying excipient, 0 to 30 weight-% of a lubricant, 0 to 10 weight-% of a plasticizer and 0 to 10 weight-% of a processing agent. In another aspect a composition is disclosed which comprises from 15 to 50 weight-% of Eudragit 4135F, at least two hydroxypropyl cellulose polymers, each having a differing molecular weight, present in a total amount of from 20 to 70 weight-%, a lubricant present in an amount of 10 to 25 weight-%, optionally a dissolution modifying excipient present in an amount of 0 to 70 weight-%, 0 to 10 weight-% of a surfactant, 0 to 10 weight-% of a plasticizer and 0 to 10 weight-% of a processing agent. The compositions are extruded, pelletized and then injection-molded. Unfortunately, most examples in the publication exhibit deficiencies, such as incomplete filling of the mold or small cracks in the capsule shells.

The International Patent Application Publication No. WO 2005/089726 discloses a composition which comprises from 10 to 80 weight-% Eudragit RL 100 or RS 100, from 20 to 70 weight-% of a dissolution modifying excipient, from 5 to 25 weight-% of a lubricant, optionally up to 10 weight-% of a surfactant, optionally up to 10 weight-% of a plasticizer and optionally up to 10 weight-% of a processing aid. The polymers Eudragit RL100 or RS100 are described by the manufacturer, Rhom Pharma, as being pH independent granules insoluble in water. The polymer Eudragit RL100 is described as being highly permeable, whereas the polymer Eudragit RS 100 is described as polymeric granule with low permeability. The compositions are extruded, pelletized and then injection-molded. Example 2 exhibited deficiencies, such as cracked or incompletely molded capsule shells. These deficient capsule shells are overcoated. However, the overcoat may determine the dissolution rate of the dosage form.

As capsules are used as dosage and delivery forms for active ingredients which have a large variety in physical conditions, e.g., solid materials of a large range of particle sizes or liquid materials of a large range of viscosities, a large range of solubilities in water, and a huge range of desired effects and dosage regimens, evidently one type of dosage form cannot fulfill all needs. Accordingly, skilled artisans are constantly searching for new dosage forms for enrichment of the art of applying active ingredients to individuals.

One object of the present invention is to provide new shells of a dosage form, such as capsules, which can be produced of good quality in the absence of a dip coating process.

A preferred object of the invention is to provide new shells of a dosage form, such as capsules, which can be produced in the absence of a dip coating process, which have a good quality such that they do not break or disintegrate during production or handling of the dosage forms, and which have a sufficiently fast disintegration after the consumption of the dosage form by an individual to allow release of the active ingredient(s) from the dosage form, such as a capsule.

A more preferred object of the invention is to provide new shells of a dosage form, such as capsules, which do not break or disintegrate during production or handling of the dosage forms but which allow a controlled release of the active ingredient(s) from the dosage form after the consumption of the dosage form by an individual.

SUMMARY

One aspect of the invention is an injection-molded shell of a dosage form which is producible by a) providing a composition comprising i) from 25 to 90 weight percent of ethylcellulose, ii) from 7.5 to 60 weight percent of a polysaccharide or polysaccharide derivative being different from ethylcellulose, and iii) from 2.5 to 50 weight percent of at least one component being different from polysaccharides and polysaccharide derivatives, based on the total weight of the composition, with the proviso that the composition comprises zero or not more than 10 weight percent of gelatin and zero or not more than 10 weight percent of a polymer comprising homo- or copolymerized acrylic acid, homo- or copolymerized methacrylic acid, a homo- or copolymerized acrylate or a homo- or copolymerized methacrylate, and b) subjecting the composition to shearing and heat to plasticize the composition and injection-molding the plasticized composition into a three-dimensional shell of a dosage form.

Another aspect of the invention is a dosage form which comprises the injection-molded shell above and one or more active ingredients.

Yet another aspect of the invention is a method of manufacturing a shell of a dosage form which comprises the steps of a) providing a composition comprising i) from 25 to 90 weight percent of ethylcellulose, ii) from 7.5 to 60 weight percent of a polysaccharide or polysaccharide derivative being different from ethylcellulose, and iii) from 2.5 to 50 weight percent of at least one component being different from polysaccharides and polysaccharide derivatives, based on the total weight of the composition, with the proviso that the composition comprises zero or not more than 10 weight percent of gelatin and zero or not more than 10 weight percent of a polymer comprising homo- or copolymerized acrylic acid, homo- or copolymerized methacrylic acid, a homo- or copolymerized acrylate or a homo- or copolymerized methacrylate, and b) subjecting the composition to shearing and heat to plasticize the composition and injection-molding the plasticized composition into a three-dimensional shell of a dosage form.

Surprisingly, it has been found that shells of a dosage form, such as capsule shells, of good quality can be made from the composition mentioned in step a) above by subjecting the composition to shearing and heat to plasticize it and by subsequent injection-molding. The shells of a dosage form, such as capsule shells, have a good quality such that they do not break or disintegrate during production or handling of the dosage forms and have a sufficiently fast disintegration after the consumption of the dosage form by an individual to allow release of the active ingredient(s) from the dosage form, such as a capsule. Moreover, it has surprisingly been found that the disintegration of the shells can be varied over a wide time period by adapting the types and weight ranges of components i), ii) and iii) of the composition for preparing the injection-molded shells, as described herein, without compromising the extrudibility and the quality of the shells. This allows the production of shells of a dosage form, such as capsule shells, which release the active ingredient in a controlled manner. Such dosage forms are called "Controlled release" or "sustained release" dosage forms. The present invention enlarges the variety of available dosage forms and opens new possibilities in health care to adjust the dosage regimen of active ingredients to the specific needs. For example, due to the present invention the shells of the dosage forms are not limited to those produced from water-soluble polymers by dip-coating, and shell thicknesses of a wide range can be produced.

DETAILED DESCRIPTION

The composition which is used for producing the injection-molded shell of a dosage form comprises at least 25 percent, preferably at least 30 percent, and more preferably at least 35 percent of ethylcellulose, based on the total weight of the composition. The composition comprises up to 90 percent, preferably up to 80 percent, more preferably up to 70 percent, and most preferably up to 60 percent of ethylcellulose, based on the total weight of the composition. Surprisingly, shells of dosage forms of good quality can be produced by injection-molding even when the concentration of ethylcellulose in the composition to be injection-molded is as low as 25 percent or as high as 90 percent. The examples below illustrate the production of capsules of good quality over a broad range of ethylcellulose concentrations. Dosage forms made from a composition with a lower concentration of ethylcellulose tend to release an active ingredient from a dosage form within a shorter time period than dosage forms made from a composition with a higher concentration of ethylcellulose. This allows the production of tailor-made dosage forms where the release of the active ingredient can be adapted to the specific dosage regimen of a given active ingredient without jeopardizing the quality of the injection-molded shells of the dosage form.The ethylcellulose preferably has an ethoxyl substitution of from 40 to 55 percent, more preferably from 43 to 53 percent, most preferably from 44 to 51 percent. The percent ethoxyl substitution is based on the weight of the substituted product and determined according to a Zeisel gas chromatographic technique as described in ASTM D4794-94(2003). The molecular weight of the ethylcellulose is expressed as the viscosity of a 5 weight percent solution of the ethylcellulose measured at 25° C. in a mixture of 80 volume percent toluene and 20 volume percent ethanol. The ethylcellulose concentration is based on the total weight of toluene, ethanol and ethylcellulose. The viscosity is measured using Ubbelohde tubes as outlined in ASTM D914-00 and as further described in ASTM D446-04, which is referenced in ASTM D914-00. The ethylcellulose generally has a viscosity of up to 400 mPa·s, preferably up to 300 mPa·s, more preferably up to 100 mPa·s, and most preferably up to 50 mPa·s, measured as a 5 weight percent solution at 25° C. in a mixture of 80 volume percent toluene and 20 volume percent ethanol. The ethylcellulose generally has a viscosity of 1.0 mPa·s or more, preferably of 2.0 mPa·s or more, more preferably of 5.0 mPa·s or more, and most preferably of 7.0 mPa·s or more, measured as a 5 weight percent solution at 25° C. in a mixture of 80 volume percent toluene and 20 volume percent ethanol. The preferred ethylcelluloses are premium grades ETHOCEL ethylcellulose which are commercially available from The Dow Chemical Company of Midland, Mich. Combinations of two or more water-insoluble polysaccharide derivatives are also useful.

Moreover, the composition comprises at least 7.5 percent, preferably at least 10 percent, more preferably at least 15 percent, and most preferably at least 20 percent, based on the total weight of the composition, of a polysaccharide or polysaccharide derivative which is different from ethylcellulose. The amount of a polysaccharide or polysaccharide derivative being different from ethylcellulose is up to 60 percent, preferably up to 50 percent, more preferably up to 40 percent, and most preferably up to 35 percent, based on the total weight of the composition. The composition may comprise more than one polysaccharide or polysaccharide derivative, provided that their total weight percentage is in the ranges stated above.

Examples of polysaccharides and polysaccharide derivatives include gum arabic, xanthan gum, gum karaya, gum tragacanth, gum ghatti, carrageenan, dextran, alginates, agar, gellan gum, gallactomannans such as guar gum, pectins, starches, starch derivatives, guar derivatives and xanthan derivatives. Starch derivatives, guar derivatives and xanthan derivatives are described in more detail in European patent EP 0 504 870 B, page 3, lines 25-56 and page 4, lines 1-30. Useful starch derivatives are for example starch ethers, such as hydroxypropyl starch or carboxymethyl starch, or "Explotab" (sodium starch glycollate). Useful guar derivatives are for example carboxymethyl guar, hydroxypropyl guar, carboxymethyl hydroxypropyl guar or cationized guar. Preferred hydroxypropyl guars and the production thereof are described in U.S. Pat. No. 4,645,812, columns 4-6. Preferred polysaccharide derivatives are cellulose esters or cellulose ethers, more preferably cellulose ethers which are different from ethylcellulose. Preferred cellulose ethers are carboxy-$C_1$-$C_3$-alkyl celluloses, such as carboxymethyl celluloses; carboxy-$C_1$-$C_3$-alkyl hydroxy-$C_1$-$C_3$-alkyl celluloses, such as carboxymethyl hydroxyethyl celluloses; $C_1$-$C_3$-alkyl celluloses, such as methylcelluloses; $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$-$C_3$-alkyl celluloses, such as hydroxyethyl hydroxypropyl celluloses, or alkoxy hydroxyethyl hydroxypropyl celluloses, the alkoxy group being straight-chain or branched and containing 2 to 8 carbon atoms. The cellulose derivatives are preferably water-soluble, which means that they have a solubility in water of at least 1 gram, more preferably at least 2 grams, most preferably at least 5 grams in 100 grams of distilled water at 25° C. and 1 atmosphere.

Particularly preferred cellulose ethers are methylcellulose, hydroxypropyl methylcellulose, hydroxyethyl methylcellulose, ethylhydroxy ethylcellulose, hydroxypropyl cellulose, and combinations of two or more of these cellulose ethers. The viscosity of these cellulose ethers preferably is from 1.2 to 200 mPa·s, more preferably from 2 to 100 mPa·s, most preferably from 2 to 50 mPa·s, measured as a 2 weight-% aqueous solution at 20° C. according to ASTM D2363-79 (Reapproved 2006).

Most preferably, the cellulose ether is a methylcellulose, in particular a methylcellulose with a methyl degree of substitution $DS_{methyl}$ of from 1.2 to 2.2, preferably from 1.5 to 2.0. The determination of the ether side groups, i.e. the $DS_{methyl}$, can be effected as described by K. L. Ketterer, W. E. Kester, D. L. Wiederrich, and J. A. Grover, Determination of Alkoxyl Substitution in Cellulose Ethers by Zeisel-Gas Chromatographie, Analytical Chemistry, Vol. 51, No. 13, November 1979, 2172-76.

Other preferred cellulose ethers are cross-linked carboxymethylcellulose or non-crosslinked carboxymethylcellulose, preferably in the form of their sodium salts. Preferably the carboxymethylcellulose is slightly cross-linked, such that it is swellable in water. Preferred cross-linked carboxymethylcelluloses are commercially available under the trademark Ac-Di Sol crosscarmellose sodium polymer from FMC BioPolymer, Philiadelphia, USA.

The composition which is used for producing the injection-molded shell of a dosage form does not comprise any amount of gelatin or not more than 10 percent, preferably not more than 5 percent, and most preferably not more than 2 percent of gelatin, based on the total weight of the composition. Most preferably, the composition does not comprise any amount of gelatin.

Moreover, the composition which is used for producing the injection-molded shell of a dosage form does not comprise any amount or not more than 10 percent, preferably not more than 8 percent, and most preferably not more than 5 percent of a polymer which comprises homo- or copolymerized acrylic acid, homo- or copolymerized methacrylic acid, a homo- or copolymerized acrylate or a homo- or copolymerized methacrylate, based on the total weight of the composition. In one embodiment of the invention the composition does not comprise any amount of such homo- or copolymer.

Moreover, the composition which is used for producing the injection-molded shell of a dosage form comprises as a component iii) at least 2.5 weight percent, preferably at least 5 weight percent, more preferably at least 10 weight percent, most preferably at least 15 weight percent, and in particular at least 20 weight percent of at least one component being different from polysaccharides and polysaccharide derivatives, based on the total weight of the composition. The amount of component iii) which is different from polysaccharides and polysaccharide derivatives is up to 50 weight percent, preferably up to 45 weight percent, more preferably up to 40 weight percent, and in particular up to 35 weight percent, based on the total weight of the composition. These one or more components iii) are preferably selected from film-forming polymers different from polysaccharides and polysaccharide derivatives or excipients which assist in melt flow, strength, and other desired injection-molding characteristics. These excipients include, but are not limited to, lubricants or glidants, plasticizers, absorption enhancers, surfactants, dissolution modifying agents, processing aids, flavouring agents, such as sweetenting agents, and dyes. The additional components are described in more detail below. The composition which is used for producing the injection-molded shell of a dosage form preferably comprises from 1 to 50 percent, more preferably from 10 to 45 percent, most preferably from 20 to 40 weight percent of a plasticizer, based on the total weight of the composition. Exemplary of plasticizers that may be employed in this invention are triethyl citrate (TEC), triacetin, tributyl citrate, acetyl triethyl citrate (ATEC), acetyl tributyl citrate (ATBC), 1,2-propylene glycol, mono-, di- and triacetates of glycerol, dibutyl phthalate, dibutyl sebacate (DBS), diethyl phthalate, vinyl pyrrolidone glycol triacetate, polyethylene glycols, glycerol, dioctyl-sodium sulfosuccinate, polyoxyethylene sorbitan monolaurate, stearyl alcohol (1-octadecanol), or castor oil; and combinations or mixtures thereof.

Incorporation of a surfactant into the composition may be desired to lower the viscosity and surface tension of the composition, preferably in an amount of from 0 to 10 percent, more preferably from 0 to 5 percent, based on the total weight of the composition. Preferred surfactants are block copolymers of ethylene oxide and propylene oxide, lecithin, sodium dioctyl sulfosuccinate, sodium lauryl sulfate (also referred to as sodium dodecyl sulfate (SDS), polyoxyethylene sorbitan fatty acid esters, i.e., the polysorbates such as Tween™, such as Tween 20, 60 & 80, the sorbitan fatty acid esters, i.e., sorbitan monolaurate, monooleate, monopalmitate, monostearate, Triton X-200, glyceryl monostearate, sucrose fatty acid esters, such as sucrose stearate, sucrose oleate, sucrose palmitate, or sucrose laurate.

The composition which is used for producing the injection-molded shell of a dosage form may also comprise one or more mold processing agents, such as one or more lubricants or glidants, preferably in an amount of from 0 to 20 percent, more preferably from 0 to 10 percent, most preferably from 0.5 to 5 percent, based on the total weight of the composition. These include but are not limited to, glycerides (oils and fats), wax and phospholipids, such as unsaturated and saturated plant fatty acids and salts thereof, such as stearates of aluminum, calcium, magnesium, zinc, and tin, stearyl alcohol, stearic acid, glycerol monostearate (GMS), talc, silicones, silicon dioxide, amorphous silicic acid, fumed silica and lecithin; and combinations or mixtures thereof.

Incorporation of a processing aid or strengthening agent, such as talc. preferably in an amount of from 0 to 10 percent, based on the total weight of the composition, may also be desired.

Moreover, the injection-molded shell of a dosage form may comprise one or more dissolution modifying agents, or substances which assist in release modifications that alter the erosion and/or swelling characteristics of the shell, preferably in a range of 0.5 to 50 percent, more preferably in a range of 2.5 to 20 percent, based on the total weight of the composition. Many different classes of agents may be used, but include those classes such as the known disintegrants represented by "Kollidon-CL", (cross-linked PVP), Kollidon VA 64 (copovidone) commercially available from BASF (Germany), low molecular weight solutes, e.g. lactose; and inorganic salts such as sodium chloride. One of more classes of dissolution modifying excipients may be used alone, or in combination as mixtures with each other, Moreover, the injection-molded shell of a dosage form may comprise other known optional adjuvants, such as colorants, anti oxidation stabilizers, flavors, processing aids, mold release agents or adjuvants to enhance the ease with which parts of shells, such as capsule bodies and caps, can be welded together, e.g. opacifier materials such as carbon, iron oxides or titanium dioxide.

Moreover, the composition which is used for producing the injection-molded shell of a dosage preferably does not comprise more than 15 percent, more preferably not more than 10 percent, most preferably not more than 4 percent, and particularly not more than 2 percent of water or an organic solvent, based on the total weight of the composition. In one embodiment of the invention the composition does not comprise any amount of water or an organic solvent. The injection-molded shell of a dosage form preferably comprises i) is from 30 to 85 weight percent, more preferably from 35 to 80 weight percent, and most preferably from 35 to 60 weight percent of ethylcellulose, ii) preferably from 5 to 50 weight percent, more preferably from 10 to 50 weight percent, and most preferably from 20 to 40 weight percent of a polysaccharide or polysaccharide derivative being different from ethylcellulose, such as methylcellulose, and iii) from 10 to 40 weight percent, more preferably from 15 to 40 weight percent, and most preferably from 20 to 40 weight percent of at least one component being different from polysaccharides and polysaccharide derivatives, based on the total weight of the composition.

In step a) of the process of the present invention components i), ii) and iii) can be blended in a conventional manner, e.g. in a mixer known in the art, such as a Henschel or a Hobart mixer. Alternatively, components i), ii) and iii) can be combined in a v-blender and subsequently subjected to roller compaction.

In step b) of the process of the present invention the above-described composition is subjected to shearing and heat to plasticize the composition. Devices for subjecting the composition to shearing and heat are well known in the art, such as single screw extruders, ram extruders, twin-screw extruders, Buss kneaders, Banbury mixers, planetary extruders, or reciprocating single-screw extruders. The composition is preferably heated to a temperature of from 100 to 250° C., more preferably from 120 to 240° C. A preferred method of subjecting the above described composition provided in step a) to shearing and heat is by hot melt extrusion. Methods for producing hot melt extrusions are well known; in these methods the selected ingredients are fed into a feed hopper of an extrusion machine. Suitable well known equipment is readily available for producing a hot melt extrusion of the blends herein, such as single screw extruders, twin screw extruders, reciprocating screw extruders, and buss kneaders.

The preferred method for producing hot melt extrusions is a single screw extruder that is part of an injection molding machine (reciprocating or continuous extrusion), ram compression molder or resin transfer molding process.

The plasticized composition is subsequently injection-molded into a shell of a dosage form, i.e. a three-dimensional dosage form having a cavity, such as a capsule. The plasticized composition preferably is not subjected to a pelletizing step before injection-molding it into a shell of a dosage form. Contrary to the teachings in US 2005/0175687 and WO 2005/089726 the plasticized composition does not require a pelletizing step between the plastification and the injection-molding step, which significantly reduces the time and capital for producing the injection-molded shells. Moreover, high stress on the composition due to pelletization and reheating of the material for injection molding can be avoided. The injection molding step b) can be conducted in a similar manner as it is generally known for the production of gelatin capsules. The production of a wide range of rigid gelatin capsule shapes and parts are described, for example, in U.S. Pat. Nos. 4,738,817; 4,576,284 and 4,738,724. The capsules can be mono- or multicompartment. The thickness of the capsules can be uniform or non-uniform, e.g. in multicompartment capsules the wall material may differ in thickness between compartments. How to produce multicompartment capsules, including those of the type where each compartment has different drug release characteristics, or for example, contains a different drug substance or formulation are also known, for example from the prior art cited on pages 1 and 2 of WO 2005/089726. The thickness of the injection-molded shell of the dosage form preferably is from 0.100 to 0.500 mm, more preferably from 0.125 to 0.400 mm One advantage of the injection-molded shells of the present invention is that a large variety of thicknesses can be produced which, e.g., can be adapted to the desired release of the active ingredient contained in the dosage form. Additionally or alternatively the shell may have one or more areas or points of weakness which preferentially dissolve and may thereby determine the time of onset and/or rate of release of the active ingredient. For example such points of weakness may comprise holes, e.g. small holes, e.g. laser-drilled holes in the shell wall, these holes being closed and/or covered with a film of a polymer material that dissolves at a pre-determined point in the digestive tract, for example an enteric polymer material. For example such points of weakness may comprise thinned parts in a shell wall formed during the molding operation in which the shell is formed.

The shell of the present invention is useful for producing a dosage form comprising the shell and one or more active ingredients, particularly for producing an oral dosage form comprising one or more active ingredients suitable for oral administration. The active ingredients contained in any capsule compartment may be present in any suitable form, e.g. as a powder, granules, compact, microcapsules, gel, syrup or liquid provided that the capsule compartment wall material is sufficiently inert to the liquid content of the latter three forms. A large variety of active ingredients, typically biologically active ingredients, are useful, such as vitamins, herbals and mineral supplements and drugs. The biologically active ingredient includes hydrophobic, hydrophilic and amphiphilic compounds. The amount of the active ingredient loaded into a dosage form will vary according to the pharmacological activity of the compound, the indication being treated, the targeted dosing regimen, the projected method of administration, the integrity or stability of the dosage form or other such reasons. The contents of the compartments, e.g. drug substances, may be introduced into the compartments by standard methods such as those used conventionally for filling capsules, such as pins for dosing or die filling. Preferably the composition is injection-molded into the shape of a capsule body and a capsule cap, the one or more active ingredients and optional additives are filled into the capsule body and the capsule cap is welded or mechanically joined to the capsule body.

EXAMPLES

The following examples are for illustrative purposes only and are not intended to limit the scope of the present invention. Unless otherwise mentioned, all parts and percentages are by weight.

The ethylcelluloses used in the examples are commercially available from The Dow Chemical Company as ETHOCEL Standard 10 Premium or ETHOCEL Standard 20 Premium ethylcellulose polymers, abbreviated as EC Std 10 and EC Std 20 in Table 1 below. Both have an ethoxyl content of 48.0-49.5%. ETHOCEL Standard 10 Premium ethylcellulose polymer has a viscosity, measured as a 5 percent solution in a solvent consisting of 80% toluene and 20% ethanol at 25° C. in an Ubbelohde viscometer, of 9-11 mPa·s. ETHOCEL Standard 20 Premium ethylcellulose polymer has a viscosity of 18-22 mPa·s.

The methylcellulose used in the examples is commercially available from The Dow Chemical Company as METHOCEL A15 cellulose ether, abbreviated as MC A15 in Table 1 below. It has a methoxyl content of 27.5-31.5% and a viscosity, measured as a 2 percent solution in water at 20° C. in an Ubbelohde viscometer, of 14-16 mPa·s.

The sodium crosscarmellose used in the examples was Ac-Di_Sol SD-711 Croscarmellose sodium NF, Ph. Eur., JP (Pharma grade), commercially available from FMC BioPolymer (Philadelphia, USA).

Glycerol, stearyl alcohol (1-octadecanol), dibutyl sebacate (DBS) and polyethylene glycol having a molar mass of 380-420 g/mol, abbreviated as PEG 400 in Table 1 below, were used as plasticizers.

Magnesium stearate was used as mold processing agent. The components in the compositions of Examples 1-7 are listed in Table 1 below.

TABLE 1

| | C-Ex 1* | C-Ex 2* | C-Ex 3* | C-Ex 4* | I-Ex 5 | I-Ex 6 | I-Ex 7 |
|---|---|---|---|---|---|---|---|
| EC Std 10 | 99.5 | 93 | | | | | 42 |
| EC Std 20 | | | 79 | 80 | 40 | 50 | |
| MC A15 | | | | | 30 | | 30 |
| Ac-Di-Sol | | 6 | | 5 | 2.5 | 15 | |
| Glycerol | | | | 10 | 5 | 30 | |
| Stearyl Alcohol | | | | 5 | 2.5 | 5 | |
| Magnesium stearate | 0.5 | 1 | 1 | | 1 | | 1 |
| Dibutyl sebacate | | | 20 | | | | 7 |
| PEG 400 | | | | | 19 | | 20 |

*Comparative Examples, but not prior art

Example 1

C-Ex 1

99.5 parts of ETHOCEL Standard 10 Premium ethylcellulose polymer and 0.5 parts of magnesium stearate were mixed in a plastic bag and then fed into a hopper of an Arburg model 221-55-250 injection molding machine with a barrel of 22 mm diameter and a 28 ton clamp mechanism. The temperature set points of the temperature control zones of the injection molding machine are shown in Table 2 where the lowest temperature is near the feed hopper and the highest temperature setting at the polymer discharge of the extruder. Pairs of mating parts of capsule shells were produced using the conditions listed in Table 2 below.

Examples 2-4

C-Ex 2 to C-Ex 4) and Example 5 (I-Ex 5

The components of the compositions listed in Table 1 above were intensely mixed in a Henschel lab mixer model FM10C equipped with a carbon steel jacketed bowl of 10 liters capacity and a three tier stainless steel blade system, running at 1705 rpm. The intense mixing caused a temperature increase of the blended materials. The jacket temperature was set at 50° C.

The mixture was subjected to injection molding with on a 50-ton FANUC ROBOSHOT injection molding machine with a 22-mm diameter barrel with the conditions listed in Table 2 below.

In Examples 1-4 (C-Ex 1 to C-Ex 4) the thickness of the produced capsule walls was about 0.38 mm (0.015 inch), the outside diameter of the capsule shells was 7.22 mm and the total length of a pair of mating parts of capsule shells was 21.72 mm, which represents typical "0" size capsules.

In Example 5 the thickness of the produced capsule walls was about 0.89 to 0.91 mm (0.035 to 0.036 inch), the outside diameter of the capsule shells was 18.95 mm and the total length of a pair of mating parts of capsule shells was 51.78 mm, which represents typical "11" size capsules.

TABLE 2

Processing Conditions for Injection Molding of Capsules

| Sample | Feed Throat °C. | Feed Zone °C. | Zones 2 and 3 °C. | | Mold Cavity °C. | Shot Size (g) | Injection Speed mm/sec | Molding Pressure (Bar) | Injection Time (sec) | Screw RPM |
|---|---|---|---|---|---|---|---|---|---|---|
| C-Ex 1* | 45 | 130 | 180 | 210 | 40 | 2 | 120 | 686 | 0.5 | 200 |
| C-Ex 2* | 45 | 160 | 170 | 180 | 40 | 2 | 120 | 686 | 0.5 | 200 |
| C-Ex 3* | 45 | 160 | 178 | 188 | 40 | 2 | 120 | 416 | 0.5 | 200 |
| C-Ex 4* | 37 | 165 | 188 | 197 | 45 | 2 | 120 | 701 | 0.5 | 200 |
| I-Ex 5  | 37 | 140 | 150 | 160 | 45 | 2 | 120 | 110 | 0.5 | 200 |

*Comparative Examples, but not prior art

Example 1 (C-Ex 1) resulted in injection molded capsules that were impossible to disintegrate within 24 hours in two aqueous buffer media having a pH of 1.2 and 5.8 respectively used for capsule disintegration testing and were not suitable for release of an active ingredient from the dosage form at any pH. Capsule disintegration testing was done by putting a steel ball of 1.04 g weight and 6.35 mm diameter inside a capsule that was suspended by a sample holder. Two aqueous buffer media were prepared as defined in USP-30. One was a KCl/HCl buffer prepared by blending 50 ml of 0.2 M aqueous KCl and 85 ml of 0.2 M aqueous HCl (pH=1.2). The other one was a $KH_2PO_4$/NaOH buffer prepared by blending 50 ml of 0.2 M aqueous $KH_2PO_4$ and 3.6 ml of 0.2 M aqueous NaOH (pH=5.8). Disintegration time was recorded as the total time from immersion of the capsule in the buffer media at 37° C. until a steel ball fell through the capsule membrane.

Example 2 (C-Ex 2) resulted in continuous production of capsules without disruption for 30 minutes but the capsules tended to be brittle and break when they were ejected from the mold. No suitable capsules for testing resulted from this formulation.

Example 3 (C-Ex 3) resulted in continuous production of high quality capsules without disruption for 30 minutes. However, again these capsules were not suitable for release of an active ingredient from the dosage form. The injection molded capsules were impossible to disintegrate within 24 hours in the two aqueous buffer media having a pH of 1.2 and 5.8 respectively used for capsule disintegration testing described above.

Example 4 (C-Ex 4) resulted in continuous production of high quality capsules without disruption for 30 minutes. However, again these capsules were not suitable for release of an active ingredient from the dosage form. The injection molded capsules were impossible to disintegrate within 24 hours in the two aqueous buffer media having a pH of 1.2 and 5.8 respectively used for capsule disintegration testing described above. Even thin films made from the composition C-Ex 4 as listed in Table 1 above had a very long disintegration time, as shown in Tables 3 and 4 below.

Example 5 (I-Ex 5) resulted in continuous production of high quality capsules without disruption for 30 minutes. The capsules in Example 5 were tested for disintegration and found to disintegrate in 396 minutes, even though they had a larger thickness than the capsules in Examples 1-4 (C-Ex 1 to C-Ex 4). The capsules in Example 5 had a thickness of 0.89 to 0.91 mm (0.035 to 0.036 inch), whereas the capsules in Examples 1-4 (C-Ex 1 to C-Ex 4) had a thickness of about 0.38 mm (0.015 inch). Controlled release capsules are often targeted to disintegrate in a time period between 6 to 11 hours. Thin films made from the composition I-Ex 5 as listed in Table 1 above had a much shorter disintegration time than comparable films of C-Ex 4, as shown in Tables 3 and 4 below.

Film Disintegration Testing

Films that had the compositions as listed in Table 1 for Examples 3-7 were produced by the melt compounding process below in order to test disintegration.

Melt compounding was conducted on a Haake MiniLab extruder. It is a conical, counter-rotating twin screw device with a recirculating loop. The barrel holds 3.5 cc of molten polymer and the recirculating loop 2.0 cc. The experiments were run at 175° C. and 100 rpm for five minutes. The temperature was controlled by three zones in the extruder and one die zone. The temperature of zone #1 was set relatively low (80° C.) to prevent material from melting and sticking in the feed throat. A flat temperature profile of 175° C. was used for extruder, zones #2, and #3. The die (zone #4) was set 10° C. hotter than the extruder profile. A 4-mm diameter rod die was attached to the extruder at the end of the barrel. The rod shaped extrudate was cut into pellets. Due to the nature of the materials, a water bath was not used to cool the strand from the extruder. Lengths of extruded materials were air cooled and cut into pellets. The pellets were then compressed into thin films under Carver Compression Molder at 177° C., and 5000 to 10,000 psi pressure.

Film disintegration was measured in two buffer media, specifically a KCl/HCl buffer medium prepared by blending 50 ml of 0.2 M aqueous KCl and 85 ml of 0.2 M aqueous HCl (pH=1.2), and a $KH_2PO_4$/NaOH buffer medium prepared by blending 50 ml of 0.2 M aqueous $KH_2PO_4$ and 3.6 ml of 0.2 M aqueous NaOH (pH=5.8), using a ball sample holder in conjunction with the dissolution test system QC-21 by Hanson Research (Chatsworth, Calif., USA). The film was subjected to controlled stress via a steel ball of 1.04 g weight and 6.35 mm diameter to simulate stomach conditions. Disintegration time was recorded as the total time from immersion of the film loaded with the steel ball in the buffer medium at 37° C. until a steel ball fell through the film membrane. All results reported were normalized based on film thickness. The procedure details are described in the reference: Zhao J, Gaynor S, Schmitt R, Coppens K, Spaulding W 2009. Mechanical, permeation, and disintegration behavior of films based on hypromellose and its blends. (Poster presented at the 2009 Annual Meeting and Exposition of the American Association of Pharmaceutical Scientists, Nov. 8-12, 2009, Los Angeles, Calif.).

TABLE 3

Film Disintegration Time in KCl/HCl buffer medium (pH = 1.2)

| Sample | C-Ex 4 | I-Ex 5 | I-Ex 6 | I-Ex 7 |
|---|---|---|---|---|
| Film thickness | 7.1 mil (0.18 mm) | 13.1 mil (0.33 mm) | 4.6 mil (0.12 mm) | 8.3 mil (0.21 mm) |
| Average disintegration Time, s | 7884 | 1866 | 1896 | 881 |
| Average disintegration Time, s/mil | 1110 | 142 | 412 | 106 |
| Average disintegration Time, s/μm | 43.7 | 5.6 | 16.2 | 4.2 |

TABLE 4

Film Disintegration Time in KH2PO4/NaOH buffer medium (pH = 5.8)

| Sample | C-Ex 4 | I-Ex 5 | I-Ex 6 | I-Ex 7 |
|---|---|---|---|---|
| Film thickness | 6.4 mil (0.16 mm) | 11.7 mil (0.30 mm) | 5.1 mil (0.13 mm) | 8.2 mil (0.21 mm) |
| Average disintegration Time, s | 5568 | 1382 | 1920 | 842 |
| Average disintegration Time, s/mil | 870 | 118 | 376 | 103 |
| Average disintegration Time, s/μm | 34.3 | 4.7 | 14.8 | 4 |

The results in Tables 3 and 4 illustrate that films prepared from compositions which are used for producing the injection-molded shells of a dosage form of the present invention (I-Ex 5 to I-Ex 7) have a much shorter disintegration time than a film prepared from Example 4 (C-Ex 4). Moreover, tailor-made dosage forms can be produced wherein the release of the active ingredient can be adapted to the specific dosage regimen of a given active ingredient without jeopardizing the quality of the injection-molded shells of the dosage form (compare I-Ex 5, I -Ex 6 and I-Ex 7).

The invention claimed is:

1. An injection-molded shell of a dosage form produced by
   a) providing a composition comprising i) from 30 to 80 weight percent of ethylcellulose having a viscosity of up to 400 mPa·s, measured as a 5 weight percent solution at 25° C. in a mixture of 80 volume percent toluene and 20 volume percent ethanol, ii) from 10 to 50 weight percent of a cellulose ether having a viscosity from 1.2 to 200 mPa·s, measured as a 2 weight-% aqueous solution at 20° C. according to ASTM D2363-79, and being selected from the group consisting of methylcellulose, hydroxypropyl methylcellulose, hydroxyethyl methylcellulose, ethylhydroxyethyl cellulose, hydroxypropyl cellulose, cross-linked carboxymethylcellulose, non-crosslinked carboxymethylcellulose, and combinations of two or more of these cellulose ethers, and iii) from 2.5 to 50 weight percent of at least one component being different from polysaccharides and polysaccharide derivatives, based on the total weight of the composition, with the proviso that the composition comprises zero or not more than 10 weight percent of gelatin and zero or not more than 10 weight percent of a polymer comprising homo- or copolymerized acrylic acid, homo- or copolymerized methacrylic acid, a homo- or copolymerized acrylate or a homo- or copolymerized methacrylate, and
   b) subjecting the composition to shearing and heat to plasticize the composition and injection-molding the plasticized composition into a three-dimensional shell of a dosage form.

2. The shell of claim 1 being a capsule shell.

3. The shell of claim 1 wherein the cellulose ether ii) is methyl cellulose.

4. The shell of claim 1 comprising i) from 35 to 70 weight percent of the ethylcellulose, ii) from 15 to 50 weight percent of the cellulose ether, and iii) from 10 to 40 weight percent of at least one component being different from polysaccharides and polysaccharide derivatives, based on the total weight of the composition.

5. The shell of claim 4 comprising i) from 35 to 60 weight percent of the ethylcellulose, ii) from 15 to 40 weight percent of the cellulose ether, and iii) from 15 to 40 weight percent of at least one component being different from polysaccharides and polysaccharide derivatives, based on the total weight of the composition.

6. The shell of claim 5 comprising i) from 35 to 60 weight percent of the ethylcellulose, ii) from 20 to 40 weight percent of methylcellulose, and iii) from 20 to 40 weight percent of at least one component being different from polysaccharides and polysaccharide derivatives, based on the total weight of the composition.

7. The shell of claim 1 wherein the composition does not comprise more than 15 percent of water or an organic solvent, based on the total weight of the composition.

8. The shell of claim 1 producible without pelletizing step between the plastification and the injection-molding step.

9. A dosage form comprising the shell of claim 1 and one or more active ingredients.

10. The dosage form of claim 9 wherein the shell is in the shape of a capsule body and a capsule cap welded or mechanically joined to the capsule body.

11. A method of manufacturing a shell of a dosage form comprising the steps of
   a) providing a composition comprising i) from 30 to 80 weight percent of ethylcellulose having a viscosity of up to 400 mPa·s, measured as a 5 weight percent solution at 25° C. in a mixture of 80 volume percent toluene and 20 volume percent ethanol, ii) from 10 to 50 weight percent of a cellulose ether having a viscosity from 1.2 to 200 mPa·s, measured as a 2 weight-% aqueous solution at 20° C. according to ASTM D2363-79, and being selected from the group consisting of methylcellulose, hydroxypropyl methylcellulose, hydroxyethyl methylcellulose, ethylhydroxyethyl cellulose, hydroxypropyl cellulose, cross-linked carboxymethylcellulose, non-crosslinked carboxymethylcellulose, and combinations of two or more of these cellulose ethers, and iii) from 2.5 to 50 weight percent of at least one component being different from polysaccharides and polysaccharide derivatives, based on the total weight of the composition, with the proviso that the composition comprises zero or not more than 10 weight percent of gelatin and zero or not more than 10 weight percent of a polymer comprising homo- or copolymerized acrylic acid, homo- or copolymerized methacrylic acid, a homo- or copolymerized acrylate or a homo- or copolymerized methacrylate, and
   b) subjecting the composition to shearing and heat to plasticize the composition and injection-molding the plasticized composition into a three-dimensional shell of a dosage form.

12. The method of claim 11 wherein the plasticized composition is not subjected to a pelletizing step before injection-molding it into a shell of a dosage form.

13. The method of claim 11 wherein the composition is injection-molded into the shape of a capsule body and a capsule cap, one or more active ingredients and optional additives are filled into the capsule body and the capsule cap is welded or mechanically joined to the capsule body.

14. The shell of claim 1 wherein the ethylcellulose i) has a viscosity from 2.0 mPa·s to 100 mPa·s, measured as a 5 weight percent solution at 25° C. in a mixture of 80 volume percent toluene and 20 volume percent ethanol.

15. The shell of claim 1 wherein the cellulose ether ii) has a viscosity from 2 to 100 mPa·s, measured as a 2 weight-% aqueous solution at 20° C. according to ASTM D2363-79.

16. The shell of claim 1 wherein the ethylcellulose i) has a viscosity from 5.0 mPa·s to 50 mPa·s, measured as a 5 weight percent solution at 25° C. in a mixture of 80 volume percent toluene and 20 volume percent ethanol and the cellulose ether ii) has a viscosity from 2 to 50 mPa·s, measured as a 2 weight-% aqueous solution at 20° C. according to ASTM D2363-79.

17. The shell of claim 6 wherein the ethylcellulose i) has a viscosity from 5.0 mPa·s to 50 mPa·s, measured as a 5 weight percent solution at 25° C. in a mixture of 80 volume percent toluene and 20 volume percent ethanol and the cellulose ether ii) has a viscosity from 2 to 50 mPa·s, measured as a 2 weight-% aqueous solution at 20° C. according to ASTM D2363-79.

\* \* \* \* \*